United States Patent [19]

DeCote, Jr.

[11] Patent Number: 4,913,146

[45] Date of Patent: Apr. 3, 1990

[54] CARDIAC SENSE AMPLIFIER WITH PATTERN RECOGNITION CAPABILITIES

[75] Inventor: Robert DeCote, Jr., Miami, Fla.

[73] Assignee: Telectronics Pacing Systems Inc., Englewood, Colo.

[21] Appl. No.: 108,777

[22] Filed: Oct. 13, 1987

[51] Int. Cl.$^4$ .............................................. A61N 1/00
[52] U.S. Cl. .............................. 128/419 PG; 128/696; 128/901
[58] Field of Search ....... 128/419 PS, 419 P, 419 PG, 128/696, 901, 419 D

[56] References Cited

U.S. PATENT DOCUMENTS

| | | | |
|---|---|---|---|
| 4,263,919 | 4/1981 | Levin | 128/901 |
| 4,478,224 | 10/1984 | Bailey | 128/901 |
| 4,494,551 | 1/1985 | Little, III et al. | 128/901 |
| 4,708,144 | 11/1987 | Hamilton et al. | 128/901 |

*Primary Examiner*—Francis Jaworski
*Assistant Examiner*—George Manuel
*Attorney, Agent, or Firm*—Gottlieb, Rackman & Reisman

[57] ABSTRACT

A cardiac sense amplifier network includes a differential amplifier, a bandpass filter, a comparator network, a microprocessor, an analog-to-digital converter, and a random-access memory. The differential amplifier is responsive to incoming electrical signals containing cardiac signals and noise signals for amplifying the electrical signals and for producing amplified electrical signals. The filter is used to filter the amplified electrical signals and for producing filtered electrical signals. The comparator network compares the filtered electrical signals with first and second reference voltages and produces a flag signal indicative of when the filtered electrical signals exceed the first or second reference voltages. The microprocessor is responsive to the flag signal for initializing the same and for generating a control signal. The analog-to-digital converter is responsive to the control signal for converting the filtered electrical signals to digital data corresponding to the cardiac signals and noise signals. The random-access-memory is used to store data representative of noise signals and for storing program instructions for causing the microprocessor to subtract the noise signals from the digital data signals in order to obtain the cardiac signals which are free of noise.

2 Claims, 2 Drawing Sheets

CARDIAC SENSE AMPLIFIER WITH PATTERN RECOGNITION CAPABILITIES

BACKGROUND OF THE INVENTION

A well-known problem associated with cardiac signal detection circuitry is that noise is oftentimes mistakenly interpreted as a cardiac signal. Typically, such noise is caused by myopotentials, the physical movement of electrode wires, and/or by high voltage electric fields in nearby power transmission lines.

Present day cardiac signal recognition circuits are virtually all based on fixed accept/reject criteria, such as specific bandpass frequencies or slew rate limits. These approaches are sub-optimal because little or no consideration is given to noise within the passband, nor to the frequently encountered idiosyncracies of a given patient's heart signal, nor to distinguishing between intrinsic and premature ventricular contractions, nor to myocardial changes related to what the patient may be doing; such as exercising, sleeping, etc.

The foregoing indicates that a real need exists for an improved cardiac signal detection system, i.e., one which is capable of automatically (a) recognizing a patient's intrinsic cardiac signal, (b) recognizing and cancelling extraneous noise, and (c) updating its recognition parameters as the patient's electrographic signature and/or the extraneous noise characteristics change with time.

This invention relates generally to a cardiac signal recognition and noise recognition/cancellation technique, and more particularly, to a cardiac sense amplifier network with capabilities for implementing these techniques. Although discussed strictly in the context of implantable pacemakers, the system described herein can be used to advantage in permanent and/or temporary pacemakers, and/or in virtually any system designed to monitor repetitive electrical signals in the presence of noise.

SUMMARY OF THE INVENTION

It is a general objective of the present invention to provide a cardiac sense amplifier system which includes a self-adaptive pattern recognition and noise recognition/cancellation circuit for reliably indicating when bona fide intrinsic cardiac signals are being sensed, and to provide these capabilities even as the cardiac signature and/or noise characteristics change with time.

It is another object of the present invention to provide a cardiac sense amplifier system which includes a differential amplifier (diff amp), a bandpass filter, a comparator network, a random access memory (RAM), and a microprocessor which includes a programmable read-only memory (PROM) with a stored program designed for processing cardiac signals such that their detection becomes relatively noise-immune.

It is another object of the present invention to provide a cardiac sense amplifier system which includes an analog-to-digital (A/D) converter, a storage device (RAM space) for storing digitized parameters obtained from incoming cardiac signals when they are known to be noise-free and an "initialize" switch in order to allow the system to accept a non-zero starting set of cardiac signal descriptors.

In accordance with the present invention, incoming electrical signals containing cardiac signals and noise signals are amplified, the amplified signals are filtered, and the filtered signals are compared with first and second reference voltages for producing a flag signal indicative of when the filtered electrical signals exceed the first and second reference voltages. The filtered electrical signals are converted to digital data signals in response to the flag signal. Data representative of noise signals is stored and is subtracted from the digital data signals in order to obtain cardiac signals which are free of noise.

In the illustrative embodiment, the diff amp is responsive to differentially sensed incoming signals (plus differential noise), while simultaneously suppressing unwanted common-mode noise. The bandpass filter enhances the signal-to-noise ratio in the bandpass of interest. The comparator network produces output flag (yes/no) signals in response to whether the amplified and filtered electrical signal exceeds either of the system's reference DC voltage levels (V+ or V−). In order to conserve power, the microprocessor is active only when the comparator output flag is high, i.e., only when the sensed signal level is large enough to warrant processing. Correspondingly, the A/D converter is activated only when the comparator flag is high and the microprocessor is programmed to make use of its output data bytes. The RAM stores transient on-line data whereas the PROM is the repository of all algorithmic instructions as required to process the incoming stream of digitized data.

BRIEF DESCRIPTION OF THE DRAWINGS

These and other objects and advantages of the present invention will become more fully apparent from the detailed description below when read in conjunction with the accompanying drawings, with like reference numerals indicating corresponding parts throughout, wherein.

DETAILED DESCRIPTION OF THE ILLUSTRATIVE EMBODIMENT

Figure 1:
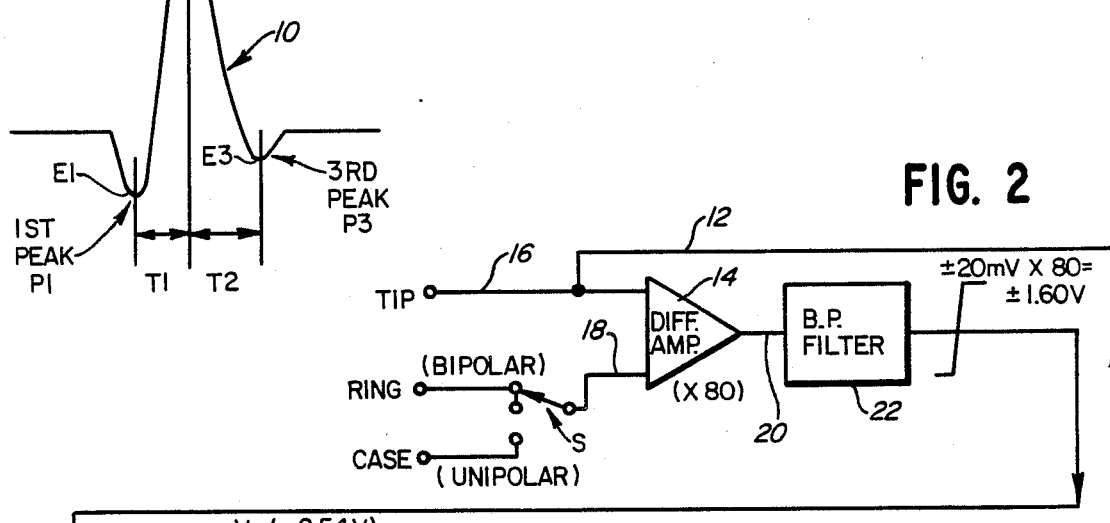
FIG. 1 is a typical filtered voltage waveform which is known to be an essentially noise-free cardiac contraction signal.

Referring now in detail to the drawings, there is shown in FIG. 1 a noise-free filtered electrogram (EGM) waveform 10 representative of a typical patient's cardiac contraction signal. This signal is resolved into a series of peaks, the key features of which are abstracted into a set of pattern recognition parameters, herein referred to as "cardiac signal waveform descriptors." For example, the set of descriptors applicable to the waveform 10 consists of the following:

1. A voltage, E1, equal to the amplitude and polarity of the first peak, P1.
2. A voltage, E2, equal to the amplitude and polarity of the second peak, P2.
3. A voltage, E3, equal to the amplitude and polarity of the third peak, P3.
4. A time interval, T1, which is equal to the time from the first peak, P1, to the second peak, P2.

5. A time interval, T2, equal to the time from the second peak, P2, to the third peak, P3.

6. A time interval, T3, not shown, equal to the time from the largest peak, P2, to the largest peak, P2', in the next waveform complex. Clearly, T3 is equal to the patient's cardiac contraction-to-contraction interval, the reciprocal of his heart rate.

In addition to the above set of six parameters is the corresponding set of six standard deviations (sigmas). These sigmas are to be evaluated using standard statistical definitions by processing the cardiac signal parameters over a prescribed number of cardiac cycles.

Thus, in this example, twelve cardiac signal waveform descriptors for filtered cardiac waveform 10 are generated by measuring the peak voltages, the time intervals therebetween, and statistically processing the entire set. These 12 pattern recognition descriptors, or any subset thereof, are initially processed by microprocessor 34 (FIG. 2) from a particular patient, stored in RAM 41, and thereafter used as a continuously updated patient generated template to determine if subsequent incoming waveforms fit the stored description of (are recognized as) his cardiac signals.

During implant, a previously determined number of cycles of filtered cardiac waveforms 10 are obtained from a patient by a physician in a noise-free environment during which time each descriptor is subjected to statistical processing by microprocessor 34 such that a mean and sigma (standard deviation) value is computed and stored in RAM 41 for each descriptor. This descriptor set allows microprocessor 34 to define a customized template which, in effect, is a compact encoded description of the particular patient's "baseline" cardiac signature. Then, each subsequent incoming waveform complex is similarly processed and each of its descriptors is compared with the corresponding stored descriptor value in order to determine whether it is within the system's given limits of acceptability for a bona fide contraction signal. Note that the user can give very wide latitude to amplitude and/or time interval changes by specifying that the appropriate system's acceptance limits be larger than the empirically determined 3-sigma values. Note also that every cardiac signal complex need not be processed. That is, in order to conserve power, the system may be designed to process only every Cth cardiac cycle. Or, if deemed desirable, a subset of the descriptors can be processed every C cardiac cycles, with the entire descriptor set processed every M cycles. The processing duty cycle finally chosen is to be based on cardiac waveform analysis research data and will involve a trade-off between reduced power consumption versus the ability to track cardiac signal descriptor changes reliably with time.

Figure 2:
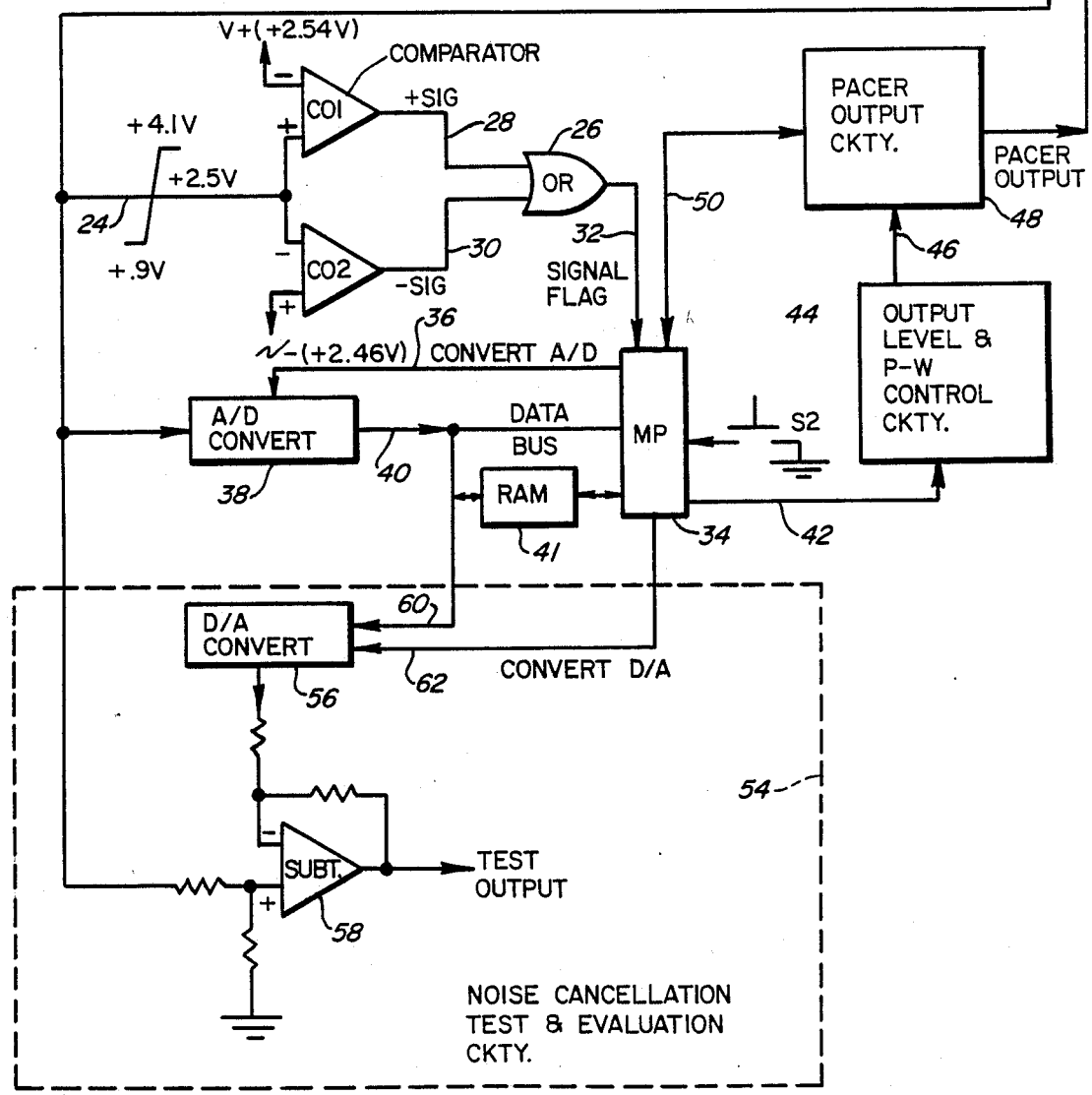
FIG. 2 is a block diagram of a proposed cardiac sense amplifier system including an independent noise cancellation test and evaluation circuit constructed in accordance with the principles of the present invention.

Referring now to FIG. 2, there is shown a block diagram of a cardiac sense amplifier system 12 constructed in accordance with the principles of the present invention. Electrically conductive wires are brought from the patient's implanted pacemaker lead system electrodes (not shown) to the terminals marked Tip, Ring and Case. As is the present practice, these electrode/lead sets serve as two-way conduits for allowing both sensing and pacing of the patient's myocardium. Also as per present practice, the incoming cardiac signals are to be sensed between the lead Tip terminal and pacer Case terminal in the unipolar configuration, or between the pacing lead's tip and ring terminals in the bipolar configuration, as determined by the position of polarity selection switch S.

Cardiac sense amplifier system 12 includes a differential amplifier 14 having one of its inputs connected to the Tip terminal via line 16 and its other input connected to either the Case or Ring electrode via line 18 and polarity selection switch S. The nominal range of peak amplitude of incoming cardiac signals is from $+/-0.5$ mV to $+/-20$ mV.

Differential amplifier 14 is designed for a passband of approximately 1 to 200 Hertz and a nominal mid-band gain of 80, as indicated. It is used for linear amplification of the incoming signals as sensed by the selected electrode pair, while simultaneously suppressing common-mode signals. This differential amplifier 14 is designed to bias both its incoming and output signals at $+2.50$ VDC so that with a nominal power supply of $+5.00$ VDC, all cardiac contraction signals will be optimally centered with the supply rails. At its extremes, this amplifier's output must handle $+/-20$ MV multiplied by the stated gain of 80, or $+/-1.60$ volts. Therefore, the dynamic range of output signal is $+2.50 +/-1.60$ VDC; or from $+0.90$ to $+4.10$ volts, as indicated on line 24.

The amplified signal from the output of differential amplifier 14 is connected via line 20 to bandpass filter 22. The bandpass filter has a peak cardiac signal frequency with a roll-off rate of 12 dB/octave on either side of the peak cardiac signal frequency. This provides rejection of both high and low frequency noise components that might be present on input lines 16 and 18. This, the output of bandpass filter 22, line 24, is an analog signal with a significantly enhanced signal-to-noise ratio for EGMs. The waveshape on line 24, in the absence of in-band noise, is typified by waveform 10 in FIG. 1.

The filtered cardiac signal from the output of bandpass filter 22, line 24, connects to a comparator network consisting of a pair of comparators CO1/CO2 and OR logic gate 26. One of the comparators, CO1, has its inverting input connected to a reference voltage V+ of $+2.54$ volts and its non-inverting input connected to the output of bandpass filter 22 on line 24. The other comparator, CO2, has its non-inverting input connected to a reference voltage V− of $+2.46$ volts and its inverting input connected to the output of the bandpass filter 22, line 24. Since the output of the bandpass filter 22 on line 24 is biased at $+2.50$ volts, the outputs of both comparators CO1 and CO2 are quiescently low. These comparators are biased to detect signals which are 40 millivolts above or below the quiescent level, respectively. In view of the fact that differential amplifier 14 provides a gain of 80, the effective signal detection level, referred to the amplifier's input terminals is $+/-(40 \text{ mV}/80) = +/-0.5$ mV. Thus, incoming noise which is outside the filter's passband, or within the filter's passband but with peak excursions of less than $+/-0.5$ millivolts, will not be sensed by either comparator, effecting a conservation of pacer battery power.

OR logic gate 26 has a first input connected to comparator CO1's output (+SIG) via line 28 and its second input connected to the output of comparator CO2 (−SIG) via line 30. The output of OR logic gate 26 is SIGNAL FLAG on line 32 which activates microprocessor 34 whenever either comparator CO1's or CO2's output is high. Thus, whenever the in-band signal input to differential amplifier 14 exceeds $+/-0.5$ millivolts SIGNAL FLAG on line 32 will be at a high logic level, causing microprocessor 34 to become activated. In turn, microprocessor 34 sends control signal CON- VERT A/D to A/D converter via line 36. This combined action initiates signal processing. Subsequently, A/D converter 38 will be receiving filtered analog signals consisting of cardiac signals plus in-band noise via line 24. It serially converts this signal to N-bit wide digital data bytes, and places them on data bus 40. RAM 41 allows the processing of the raw data bytes into the aforementioned signal descriptors and stores the data bytes representing the resultant descriptor set.

INIT switch 52 is provided for loading the system with the initial non-zero cardiac signal descriptors while in a known noise-free environment, as previously discussed. When INIT switch S2 is closed, the next ten or more cardiac cycles will be used in order to compute the original mean and sigma values for each descriptor, and the resultant set will be stored in RAM 41. During this initialization phase, the pacer will be functioning in a 30 ppm backup mode with sense/pace decisions aided only by bandpass filter 22, as in most present-day pacing systems. That is, if no cardiac activity is sensed for a prescribed time (2 seconds in this example), microprocessor 34 issues a control signal on line 42 to pacer output level and pulsewidth control circuit 44, whose output, in turn, is fed to pacer output circuit 48 via line 46. Pacer output circuit 48 is also controlled in an on/-off manner directly by microprocessor 34 via line 50. Output level and pulsewidth control circuit 44 and pacer output circuit 48 may be of conventional design, which are well-known to persons skilled in the art.

Once initialized, the cardiac signal recognition descriptors stored in RAM 41 will be automatically and continuously updated over the most recent C noise-free cardiac cycles. The criterion for "noise-free" signal within any cardiac cycle is that its incoming descriptors are all within the limits defined by the means, sigmas, and multipliers currently stored in RAM 41, as discussed in detail below. Because the cardiac recognition descriptors are always based on the most recent set of N noise-free cardiac cycles, they will automatically track and update the patient's cardiac action as he exercises, sleeps, etc., on an on-going beat-by-beat (or, Xth-beat by Xth beat) basis.

To mentally visualize how the components of the cardiac signal recognition descriptors relate, think of the set of mean values as defining a baseline signal recognition template, of the associated sigmas as providing an empirical measure of looseness-of-fit for each of the template's elements, and of the user defined coefficients as specifying the system's acceptable looseness-of-fit limits for each of the template's elements. These functional tie-ins can be readily discerned in the equations below:

$$T1 = T1' +/- N1\ \text{Sigma}(T1)$$

$$T2 = T2' +/- N2\ \text{Sigma}(T2)$$

$$T3 = T3' +/- N3\ \text{Sigma}(T3)$$

$$E1 = E1' +/- N4\ \text{Sigma}(E1)$$

$$E2 = E2' +/- N5\ \text{Sigma}(E2)$$

$$E3 = E3' +/- N6\ \text{Sigma}(E3)$$

Where, each of the unprimed terms (T1 to E3) represents a range as specified by the system's acceptable upper and lower descriptor limits; the primed terms (T1' to E3') represent the mean value for each descriptor; the Sigma terms (Sigma(T1) to Sigma (E3)) represent the calculated empirical standard deviation for each descriptor; and the coefficients (N1 to N6) allow the user to specify the system's acceptable looseness-of-fit limits in that they serve as multipliers applied to each sigma. Thus, for example, since N3 represents the looseness-of-fit coefficient for the cardiac rate interval (T3), the cardiologist may elect to program it fairly tight at, say, N3=1.5, or medium at N3=2.5, or loose at N3=3.5; depending on the patient's history of arrythmia patterns. In fact, by way of further example, if the patient is known to have a very high degree of arrythmia, the cardiologist may elect to eliminate rate as a signal descriptor altogether by programming T3 "Off."

As for establishing optimal user defined acceptable looseness-of-fit coefficients for each cardiac signal descriptor, some prior waveform analysis research with a specially designed Holter-type monitor backed up by pattern recognition and statistical evaluation software will have to be undertaken on patients with "classical" cases of cardiac malfunction. The data so obtained is to be computer processed in a manner that is compatible with the pattern recognition algorithms discussed above so that it will subsequently allow cardiologists to quantify how each of the aforementioned sigmas behaves in each type of patient; when he's at rest, as he goes from rest to exercise, and as he participates in other myocardial influencing activities.

Clearly, a desirable objective for these studies would be a baseline or "stat" set of descriptors, proven to be totally safe with all patients. It should also be clear from the above that the tighter the template is made, the better the system's noise immunity, but concomitantly, the higher the probability of not being able to track cardiac signal changes and/or of mistakenly refusing to acknowledge irregular bona fide cardiac contraction signals. This trade-off of noise immunity versus false negative responses is inherent in the specification of user defined coefficients (N-values).

Self-Adaptive Noise Recognition Capabilities

The foregoing discussion has focused exclusively on noise-free EGMs and their processing. The following disclosure will examine what may be done with sense amplifier 12 in the presence of noise. However, one must first distinguish between random noise and short-term stationary noise. For example, random noise may be due to a patient's muscle movements, i.e., random myopotentials. It follows that since there is no pattern to it, there is no predictability to it and, therefore, no logical algorithm can do much to combat it. However, short-term stationary noise is another matter. For example, 60 Hz power line nose is a classic example of stationary noise. The system described above can (a) recognize this type of noise and (b) implement a noise-cancelling algorithm against it.

In general, any incoming voltage waveform which trips comparators CO1 or CO2, but does not qualify as a cardiac signal is to be tentatively considered to be probable stationary noise. Such waveforms will be examined for periodicity in terms of their zero crossings. If zero crossings are uniformly spaced, periodicity exists, and if the signal's amplitude and waveshape are essentially constant over several cycles, the signal is said to be short-term stationary. In such cases, the system will store a complete cycle of the waveform in RAM. Note that the noise pattern recognition algorithm can function quite effectively in the relatively quiet intervals between cardiac contractions.

For simplicity, it will be assumed that the extraneous signal is pure 60 Hz. Once its periodicity is verified, the system store a noise template which consists of one cycle of the incoming 60 Hz. Thereafter, it simply tracks the amplitude and phase (peaks and zero crossings) of the incoming extraneous signal. When an abrupt break in sensed amplitude and/or phase occurs, the system will subtract the properly phased noise template's waveshape from the incoming signal and apply the patient's EGM pattern recognition descriptor algorithms to the result. The operative idea here is simply: (Signal+Noise)−(Noise)=Signal.

Thus, a high level of immunity to stationary noise is clearly possible. In contrast, when present-day pacemakers detect stationary noise, they go into an asynchronous pacing mode (VOO), at the risk of thereby inducing cardiac fibrillation is some patients.

Noise Cancellation Test and Evaluation Circuitry

The proposed noise cancellation test and evaluation circuit 54 in FIG. 2 is included for evaluating the above system's stationary noise cancellation performance. It will prove useful for system development, testing, evaluation, and troubleshooting. However, it is to be clearly understood at the outset that this test and evaluation circuit and the required special software discussed below are wholly independent of, and external to sensing system 12, as discussed above.

Test and evaluation circuit 54 includes D/A converter 56 and op amp 58; which is configured as a subtraction amplifier. D/A converter 56 has a first input consisting of N data bits on line 60 from the system's data bus. The other input to D/A converter 56 is the CONVERT D/A control signal on line 62 from microprocessor 34. Subtraction amplifier 58 has the output of D/A converter 56 as one of its inputs and the output of the bandpass filter, line 24, as its other input.

During test and evaluation of the system's noise cancellation capabilities, the input to sense amplifier 12 will consist of a noise-free cardiac signal plus a controlled amount of stationary noise. This composite (signal+-noise) waveform will be provided by a noise loading test set, as discussed below. For this test, special software within microprocessor 34's PROM will control matters such that the D/A converter's output will be the aforementioned stored stationary noise template. Thus, one input to subtraction circuit 58 will be the system's rendition of the stationary noise template, and the other input will be the incoming composite test signal, from line 24. Evidently, under these conditions, the ideal output of subtraction circuit 58 will be a noise-free representation of the cardiac signal, i.e., (Signal+-Noise)−(Noise)=Signal.

Noise-Loading Test and Evaluation Circuitry

Figure 3:
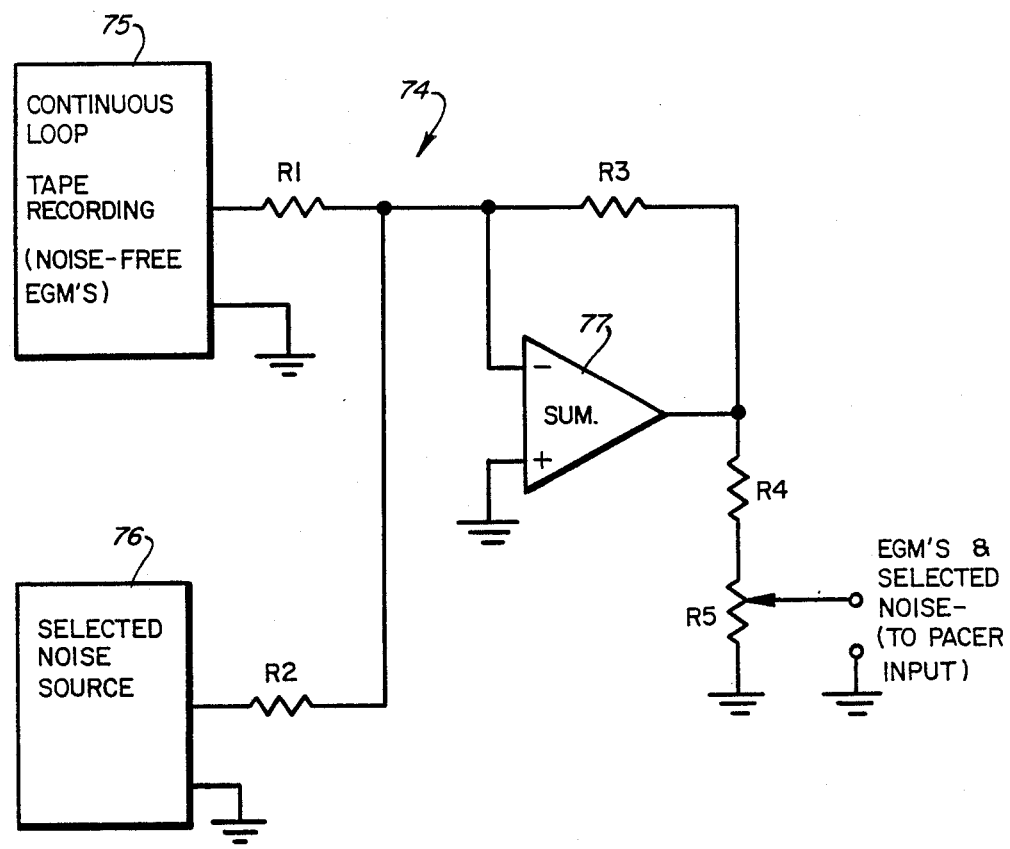
FIG. 3 is a block diagram of a proposed noise-loading test set used for performing controlled signal-to-noise ratio tests, also constructed in accordance with the principles of the present invention.

A proposed test and evaluation circuit 74 is provided in FIG. 3 for making signal-to-noise ratio measurements on any cardiac sense amplifier. This circuitry will prove useful in system development, testing, evaluation, troubleshooting, and performance comparisons. However, it is to be clearly understood at the outset that this noise-loading test and evaluation circuit is wholly independent of and external to sensing system 12, as discussed above.

Test and evaluation circuit 74 includes a continuous loop tape recording of noise-free EGMs 75, a selected noise source 76, and an op amp 77, which is configured as a summing amplifier. The continuous loop noise-free EGMs may be as recorded directly from a patient's heart or may be any electronically synthesized waveform, as from a commercially available waveform generator or from a suitably programmed microprocessor working into a D/A converter. In any case, the objective is to have a convenient source of statistically stationary noise-free EGMs whose descriptor set can be accurately specified at the output of bandpass filter 22, line 24. Thus, with noise-free signals whose descriptors are well-known the user will be in a good position, prior to the introduction of noise, to determine whether the algorithms incorporated in microprocessor 34 in fact provide acceptably accurate values for its descriptor set.

The continuous loop tape recording 75, together with the selected noise source 76, plus resistors R1, R2, R3 and summing amplifier 77, are configured to provide the required (Signal+Noise) summing action. The selected noise source allows the introduction of controlled levels of (a) simulated or recorded power line noise, or (b) simulated or recorded myopotentials, or (c) simulated or recorded PVCs, or (d) broadband noise, or (e) just about any other extraneous noise source which the user may care to introduce. At the output of summing amplifier 77, resistors R4 and R5 provide composite signal attenuation, with R5 allowing a fine adjustment of the net signal level fed to the system under test. Thus, the user can readily measure the noise-free EGM amplitude as well as the extraneous noise level amplitude, and thus accurately quantify the signal-to-noise ratio operative at the input to the sense amplifier. If desired, conventional bandpass filter only, cardiac signal amplifiers can also be tested in this set-up for performance comparisons.

Although an illustrative embodiment of the invention has been shown and described, it is to be understood that various modifications and substitutions may be made by those skilled in the art without departing from the novel spirit and scope of the present invention.

What is claimed is:

1. A cardiac sense amplifier network comprising:
 means responsive to incoming electrical signals containing cardiac signals and noise signals for amplifying said electrical signals;
 filter means for filtering said amplified electrical signals;
 comparator means for comparing said filtered electrical signals with first and second reference voltages and for producing a flag signal indicative of when said filtered electrical signals exceed said first or second reference voltages;
 said comparator means comprising a first comparator, a second comparator, and an OR logic gate;
 digital data processing means being responsive to said flag signal for initializing said processor means and for generating a control signal;
 analog-to-digital converting means responsive to said control signal for converting said filtered electrical signals to digital data signals corresponding to said cardiac signals and said noise signals; and
 storage means for storing data representative of noise signals and for storing program instructions for causing said processing means to subtract said noise signals from said digital data signals in order to obtain said cardiac signals which are free of noise.

2. A cardiac sense amplifier network as claimed in claim 1, wherein said first comparator has its inverting input connected to receive the first reference voltage and its non-inverting input connected to receive said filtered electrical signals, said second comparator has its non-inverting input connected to receive the second reference voltage and its inverting input connected to receive said filtered electrical signals, and said logic gate has its first input connected to the output of said first comparator, its second input connected to the output of said second comparator, and an output producing the flag signal.

* * * * *